United States Patent
Romero et al.

(10) Patent No.: US 7,850,997 B2
(45) Date of Patent: Dec. 14, 2010

(54) DIETARY COMPOSITIONS AND METHODS OF ENHANCING LEAN BODY MASS AND EXERCISE PERFORMANCE

(76) Inventors: Tim Romero, 201 Fieldend St., Suite A, Sarasota, FL (US) 34240; Peter Miller, 13439 Antlers St., Broomfield, CO (US) 80020

( * ) Notice: Subject to any disclaimer, the term of this patent is extended or adjusted under 35 U.S.C. 154(b) by 441 days.

(21) Appl. No.: 12/052,940

(22) Filed: Mar. 21, 2008

(65) Prior Publication Data

US 2008/0233186 A1    Sep. 25, 2008

Related U.S. Application Data

(60) Provisional application No. 60/896,049, filed on Mar. 21, 2007.

(51) Int. Cl.
*A61K 33/00* (2006.01)
*A61K 9/68* (2006.01)
*A01N 37/12* (2006.01)

(52) U.S. Cl. .................. 424/718; 424/440; 514/561

(58) Field of Classification Search .............. None
See application file for complete search history.

(56) References Cited

U.S. PATENT DOCUMENTS

| | | | |
|---|---|---|---|
| 6,004,926 A | 12/1999 | Shimizu et al. | |
| 6,124,277 A | 9/2000 | Schacht et al. | |
| 6,127,165 A | 10/2000 | Anderson et al. | |
| 6,368,617 B1 | 4/2002 | Hastings et al. | |
| 6,727,076 B2 | 4/2004 | Bochner | |
| 6,784,209 B1 | 8/2004 | Gardiner et al. | |
| 6,812,249 B2 | 11/2004 | Abraham et al. | |
| 6,967,102 B1 | 11/2005 | Anderson et al. | |
| 7,138,134 B2 | 11/2006 | Wang et al. | |

OTHER PUBLICATIONS

Inhibition o fNitric Oxide Synthase Disrupts Inhibitory Gating of Auditory Responses in Rat Hippocampus (1998).
Effects of guanidino compounds on the endothellum-derived relaxing factor Inhibitor NG-monomethyl L-argine (1991).
Nitric-oxide production and neurotoxicity mediated by activated microgila from human versus mouse brain. (1994).
On the linkage between AMPA and NMDA receptor-mediated EPSPs in homosynaptic long-term depression in the hippocampai CA1 region of young rats (1995).
The influence of nitric oxide in perigeniculate GABAergic cell activity in the anesthetized cat. (1996).

*Primary Examiner*—Robert A Wax
*Assistant Examiner*—Jeffrey T Palenik
(74) *Attorney, Agent, or Firm*—Gifford, Krass, Sprinkle, Anderson & Citkowski, P.C.

(57) ABSTRACT

Various compounds can be administered orally to humans or animals for the purpose of enhancing nitric oxide production. Enhancing nitric oxide production is beneficial for those looking to increase lean body mass or enhance exercise performance. Such administration can also be used for the purpose of enhancing nutrient transport for purposes of athletic performance and controlling bodyweight and body fat levels. L-Arginine and alpha amino n-Butyrate work synergistically to enhance nitric oxide production and may further be coupled with either and/or a) an inhibitor of nitric oxide breakdown or b) a nitric oxide potentiators or other precursor and serve to accomplish this goal of enhance nitric oxide. The composition may be administered in a variety of ways including capsules, tablets, powdered beverages, bars, gels or drinks.

16 Claims, No Drawings

DIETARY COMPOSITIONS AND METHODS OF ENHANCING LEAN BODY MASS AND EXERCISE PERFORMANCE

CROSS REFERENCE TO RELATED APPLICATIONS

The present application claims priority from U.S. Provisional Application No. 60/896,049, filed on Mar. 21, 2008. The disclosure of which is incorporated by reference.

FIELD OF THE INVENTION

Disclosed herein is an embodiment(s) of a dietary supplement including L-Arginine alpha amino-N Butyrate. The dietary supplement may also include additional nitric oxide enhancing compounds. Also disclosed herein are methods of enhancing nitric oxide production, in humans and animals, for enhancing lean body mass and exercise performance.

BACKGROUND OF THE INVENTION

As will be mentioned further infra, one of the first discoveries relating to the role of nitric oxide role was arrived at in an attempt to identify the agent responsible for promoting blood vessel relaxation and regulating vascular tone. This agent, endothelium-derived relaxing factor (EDRF), was assumed to be a protein similar to other known signalling molecules. The discovery that EDRF was in fact nitric oxide, a small gaseous molecule—led to additional interest and research in the field.

Nitric Oxide is a very short lived molecule, having a half life of only a few seconds. Nitric Oxide may diffuse rapidly across cell membranes. Furthermore, depending on environmental conditions, Nitric Oxide may act on elements that may be at a distance of several hundred microns from the site of Nitric Oxide production.

Nitric Oxide is produced by enzymes known as nitric oxide synthases of which there are three types—Inducible (iNOS), endothelium (eNOS) and neuronal (nNOS). Each enzyme acts on various target tissues.

A mode of action for Nitric Oxide is to stimulate guanylate cyclase, leading to an increase in intracellular cyclic GMP in target cells. This, in turn, may lead to further effects, depending on the cell.

Nitric Oxide is synthesised from L-arginine by the action of Nitric Oxide synthase (NOS), with the production of L-citrulline. L-Citrulline may then be recycled to L-arginine by argininosuccinate synthetase and argininosuccinase in a cycle that allows it to be reused continuously. However, both oxygen and NADPH are required in order for the recycling process to occur.

The nitric oxide (NO) system has been the subject of much study in recent years, due to the numerous discoveries on its actions and effects in the body.

In 1991, Moncasa et al. indicated that the nitric oxide is produced by the endothelium of blood vessels and assists in the regulation of vascular tone/blood pressure. Then, again in 1991, Snyder and Bredt indicated that nitric oxide was manufactured in many tissues including, but not limited to, the central and peripheral nervous systems.

Later, in 1993, Garthwaite observed that nitric oxide played a role in neural signaling.

In 1999, Marechal and Gailly found that nitric oxide has an important role in mechanical and metabolic muscle power.

Then, in 2003, Narin et al. indicated that regular aerobic exercise may result in an increase in blood concentrations of nitrite oxide. Nitric oxide is thus an important signaling molecule that acts in many tissues and offers a diverse range of physiological processes.

Rector et al. reports that in 1996, patients in a double-blind study having moderate to severe heart failure were given 6 weeks of oral arginine (5.6 to 12.6 g/day) and 6 weeks of matched placebo capsules in random sequence.

In 2001, Nagaya et al. reported that compared with placebo, arginine significantly increased forearm blood flow during forearm exercise. Specifically, patients with primary or precapillary secondary pulmonary hypertension were given a placebo or oral arginine (0.5 g/10 kg or 3.5 g for a 70 kg person) for one week. Arginine was found significantly decreased, versus placebo, the mean pulmonary arterial pressure and pulmonary vascular resistance, indications that arginine causes pulmonary vasodilation.

In another 2001 study, Marchesi et al. evaluated endothelial function (expressed as flow-mediated vasodilation [FMV]) in 7 healthy males. On day one, measurements were made at baseline and 2, 4 and 6 hours after a standardized oral fat load. Arginine (6 g/day) was then given for 10 days and the same measurements were taken an day 11. After the first oral fat load, FMV significantly decreased at 2 and 4 h, and overlapped with the basal levels at 6 h. After arginine treatment, FMV significantly decreased at 2 h and normalized after 4 and 6 h. As such, the authors concluded that postprandial endothelial impairment is partly abolished by arginine administration.

In 2000, Bednarz at al, reported that arginine supplementation increased endurance. For example, 25 patients with stable coronary artery disease underwent two separate exercise tests after they were given a placebo or 6 g oral L-arginine for 3 days. In summary, arginine was found to significantly increased exercise duration.

Then in 1997, Ceremuzynski et al. found that the administration of oral L-arginine (6 g) for 3 days increased exercise capacity in 22 patients with stable angina pectoris and healed myocardial infarction compared Nitric oxide as it relates to sports performance dilates and opens blood vessels through eNOS enhancement, which allows for a increased transport of nutrients into the cell. Users have reported a "pumped" effect showing that more blood is being drawn into the muscle. This effect, while quite superficial may have implications in numerous sports. As blood flow goes, the amount of nutrients delivered to the tissues impacts numerous aspects of athletic performance, including the rate of protein synthesis, compartmentalization of blood glucose, nutrient partitioning and numerous other pathways.

Nitric Oxide has also become a targeted approach for those looking to enhance lean body mass and exercise performance. Products on the market that claim this benefit contain various forms of L-Arginine.

Arginine has been shown in some research to increase levels of Nitric oxide. However, the doses administered in research are very high, resulting in unwanted side effects. The administration of L-Arginine in the enhancement of nitric oxide is somewhat limited in these aspects. Thus, there is a need for a more viable method and composition for enhancing nitric oxide.

SUMMARY OF THE INVENTION

Disclosed herein is: (a) dietary composition comprising L-Arginine alpha amino n-Butyrate and b) methods of to enhancing nitric oxide production, in humans and animals, for enhancing lean body mass and exercise performance.

Arginine is a metabolic precursor to nitric oxide. Therefore, Arginine is preferred when seeking to supply substrates necessary for nitric oxide production. However, as will be discussed later on in the invention, the particular form of arginine disclosed herein has not been used, and it has been found to possess unique intrinsic properties.

DETAILED DESCRIPTION OF THE INVENTION

Disclosed herein is a dietary supplement including L-Arginine alpha amino n-Butyrate, a direct metabolic substrate to nitric oxide (NO) production. L-Arginine alpha amino n-Butyrate also directly supplies a body with physiologically relevant substrates to nitric oxide production. The supplemental may be prepared in a variety of forms including, for example, a powder, a liquid, a tablet, a capsule, a pill, a candy, a confection food additive or a gel cap. Disclosed herein is a dietary supplement may include a concentration range of L-Arginine alpha amino n-Butyrate between 1 g-10,000 g. However a more preferred range for L-Arginine alpha amino n-Butyrate is from 100 g-5000 g. A still more preferred range being from 500 g-3000 g.

Arginine ($C_6H_{14}N_4O_2$-chemical name 2-amino-5-guanidinovaleric acid) is nonessential amino acid produced by the hydrolysis or digestion of proteins. It is one of the hexone bases and supplies the amidine group for the synthesis of creatine. Arginine is also formed by the transfer of a nitrogen atom from aspartate to citrulline in the urea cycle. It then gives off urea, to form ornithine.

Arginine may be used in a physiologically active form which is designated as the "L" form. L-arginine in the composition is free of other amino acids, peptides and proteins that would interfere with the uptake of L-arginine into the animal's system.

As mentioned supra, the dietary supplement includes L-arginine alpha amino n-Butyrate. The combination of both L-Arginine and alpha amino-n-Butyate may occur via a simple mixture, or though chemical bonding functions.

In another embodiment of the dietary supplement, the supplement may include L-arginine alpha amino n-Butyrate in combination with additional compounds to further enhance the output of nitric oxide production.

An increase in nitric oxide system results from the increase in the quantity of nitric oxide in the system, or from an improvement in the level of activity of the nitric oxide system, or by some other means. Particular compositions that have been showing to increase the quantity of nitric oxide in the system (i.e., a direct stimulator of nitric oxide) include Gynostemma Pentaphyllum. Likewise, Rutaecarpine directly stimulates nitric oxide production. Other compounds that are well know in the art are also available to increase nitric oxide production.

Additional nitric oxide potentiators or precursors that may be used in connection with the disclosed dietary supplement include: gypenosides (Gynostemma pentaphyllum), Rutaecarpine, 4-Butrybetaine, perillaldehyde Ginseng, or another derivate of L-Arginine (L-Arginine base, L-Arginine Hydrochloride, L-Arginine Pyroglutamate, Arginine Esters, L-Arginine Isocaproate, L-Arginine Alph-Ketoglutarate, and mixtures thereof) or L-Citrulline (Base, L-Citrulline Malate, Citrulline Esters, L-Citrulline AICG, and mixtures thereof).

In another embodiment of the dietary supplement, the supplement may include L-arginine alpha amino n-Butyrate in combination with additional compounds to further enhance the output of nitric oxide production and/or in combination with additional compounds that to inhibit the breakdown of nitric oxide, thus enhancing its biological activity.

As mentioned supra, since nitric oxide is a short lived gas, the ability to mitigate the breakdown of nitric oxide is a key component of the disclosed supplement. Coupled with a substrate and/or an enhancer of nitric oxide production, compounds that may enhance the active life of nitric oxide would serve tremendous benefit.

A particular composition that has been shown inhibit the breakdown of nitric oxide includes Pomegranate or an extract or a derivative thereof, which was recently been of interest as an antioxidant. Pomegranate general health effects are known to increase overall antioxidant status.

Pomegranate's affects as an antioxidant is mediated by protecting the body against harmful reactive oxygen species. Of particular interest is one component of the reactive oxygen species. The superoxide anion is an important key pre-oxidant in that functions to breakdown the biological action of nitric oxide. Through this mechanism, the biological activity of nitric oxide may be maintained by inhibiting its breakdown.

Other compositions that have been shown inhibit the breakdown of nitric oxide include L-Norvaline, blueberry or an extract or a derivative thereof, grape seed or an extract or a derivative thereof, or red wine or an extract or a derivative thereof.

Also, as it relates to the methods of the invention, and the end goal of enhancing lean body mass through various interventions to ultimately enhance and maintain the output of nitric oxide, nitric oxide has been shown to amplify growth signals. One of the roles of nitric oxide is to mediate satellite cell activation. After muscle injury, including resistance exercise, satellite cells are activated and recruited to cycle as precursors for new muscle formation. Between injury and proliferation in vivo, satellite cells express immediate early genes after 3-6 hours and muscle regulatory genes after 6 hours. The expression of these genes, release of growth factors such as bFGF, and DNA synthesis 24-30 hours later are used to characterize muscle regeneration in injured and dystrophic muscle. The release of HGF, the one growth factor that activates quiescent satellite cells in vitro and in vivo, is dependent on nitric oxide production. Accordingly, it will be appreciated the dietary supplement, specifically a therapeutically effective amount of L-Arginine and alpha amino n-butyrate, may be orally administered to a mammal for the purpose of enhancing lean body mass.

Furthermore, related to muscle growth, nitric oxide increases contractile force within the muscle cell. Specifically, nitric oxide effects muscle by increasing the shortening velocity of loaded or unloaded contractions. Nitric oxide also improves mechanical and metabolic muscle power, similar to a transformation of slow-twitch to fast-twice muscle. Nitric oxide is expressed equally in fast- and slow-twitch fibers of some human skeletal muscles. In the muscle, nitric oxide increases maximal velocity of shortening. Accordingly, it will again be appreciated the dietary supplement, specifically a therapeutically effective amount of L-Arginine and alpha amino n-butyrate, may be orally administered to a mammal for the purpose of enhancing muscle growth and mass.

Example formulations for the disclosed dietary supplement are provided infra:

| EXAMPLE 1 | |
|---|---|
| Arginine alpha amino n-Butyrate | 2,000 mg |
| Norvaline | 400 mg |
| Arginine Alpha-ketogluturate | 3,000 mg |

EXAMPLE 2

| Arginine alpha amino n-Butyrate | 3,000 mg |
|---|---|
| Creatine Monohydrate | 5,000 mg |
| Beta-Alanine | 1,000 mg |
| Arginine Alpha-ketogluturate | 2,000 mg |

EXAMPLE 3

| Arginine alpha amino n-Butyrate | 1,000 mg |
|---|---|

EXAMPLE 4

| Arginine alpha amino n-Butyrate | 500 mg |
|---|---|
| HMB | 1,500 mg |
| arginine alpha-ketogluturate | 3,000 mg |
| arginine keto-isocaproate | 500 mg |
| Grape Seed Extract | 50 mg |
| Resveratrol | 50 mg |

EXAMPLE 5

| Arginine alpha amino n-Butyrate | 500 mg |
|---|---|
| Gamma Butyrobetaine | 100 mg |
| Gynostemma Pentaphyllum (gypenosides) | 100 mg |
| arginine pyroglutamate | 500 mg |
| Magnesium Tashinoate B | 25 mg |
| Rutaecarpine | 50 mg |

Having thus described certain embodiments of the invention, various other embodiments will become apparent to those having skill in the art that to no depart from the scope of the claims.

I claim as my invention:

1. A composition comprising L-Arginine alpha amino n-butryate.

2. The composition of claim 1 wherein L-Arginine and alpha amino n-butyrate are blended together.

3. The composition of claim 1 wherein L-Arginine and alpha amino n-butyrate are chemically bonded.

4. The composition of claim 1 further comprising a nitric oxide potentiator or precursor.

5. The composition of claim 4 wherein the nitric oxide potentiator or precursor is selected from a group consisting of: gypenosides (Gynostemma pentaphyllum), Rutaecarpine, 4-Butrybetaine, perillaldehyde Ginseng, or another derivate of L-Arginine (L-Arginine base, L-Arginine Hydrochloride, L-Arginine Pyroglutamate, Arginine Esters, L-Arginine Isocaproate, L-Arginine Alph-Ketoglutarate, and mixtures thereof) or L-Citrulline (Base, L-Citrulline Malate, Citrulline Esters, L-Citrulline AICG, and mixtures thereof).

6. A composition according to claim 1 further comprising a nitric oxide breakdown inhibitor.

7. The composition of claim 6 wherein the a nitric oxide breakdown inhibitor is selected from a group consisting of: L-Norvaline, pomegranate or an extract or a derivative thereof, blueberry or an extract or a derivative thereof, grape seed or an extract or a derivative thereof, or red wine or an extract or a derivative thereof.

8. A composition of claim 1, wherein the composition is prepared in a form selected from a group consisting of: a powder, a liquid, a tablet, a capsule, a pill, a candy, a confection food additive or a gel cap.

9. A method of increasing the lean body mass in a mammal comprising the step of orally administering to a mammal, a therapeutically effective amount of L-Arginine and alpha amino n-butyrate.

10. A method of claim 9, further comprising the step of: orally administering to a mammal, a composition comprising a therapeutically effective amount of L-Arginine and alpha amino n-butyrate, a nitric oxide precursor, and a nitric oxide potentiator and a nitric oxide breakdown inhibitor.

11. A composition consisting essentially of L-Arginine alpha amino n-butryate, a nitric oxide potentiator or precursor, and a nitric oxide breakdown inhibitor.

12. The composition of claim 11 wherein the nitric oxide potentiator or precursor is selected from a group consisting of gypenosides (Gynostemma pentaphyllum), Rutaecarpine, 4-Butrybetaine, perillaldehyde Ginseng, or another derivate of L-Arginine (L-Arginine base, L-Arginine Hydrochloride, L-Arginine Pyroglutamate, Arginine Esters, L-Arginine Isocaproate, L-Arginine Alph-Ketoglutarate, and mixtures thereof) or L-Citrulline (Base, L-Citrulline Malate, Citrulline Esters, L-Citrulline AICG, and mixtures thereof).

13. The composition of claim 11 wherein the a nitric oxide breakdown inhibitor is selected from a group consisting of: L-Norvaline, pomegranate or an extract or a derivative thereof, blueberry or an extract or a derivative thereof, grape seed or an extract or a derivative thereof, or red wine or an extract or a derivative thereof.

14. A composition according to claim 11, wherein the composition is prepared in a form selected from a group consisting of: a powder, a liquid, a tablet, a capsule, a pill, a candy, a confection food additive or a gel cap.

15. The composition of claim 11 wherein L-Arginine and alpha amino n-butryate are blended together.

16. The composition of claim 11 wherein L-Arginine and alpha amino n-butryate are chemically bonded.

* * * * *

UNITED STATES PATENT AND TRADEMARK OFFICE
CERTIFICATE OF CORRECTION

PATENT NO. : 7,850,997 B2
APPLICATION NO. : 12/052940
DATED : December 14, 2010
INVENTOR(S) : Tim Romero et al.

Page 1 of 1

It is certified that error appears in the above-identified patent and that said Letters Patent is hereby corrected as shown below:

At column 2, line number 1, delete "nitrite", insert --nitric--

At column 2, line number 22, delete "an", insert --on--

At column 2, line number 34, delete "increased", insert --increase--

At column 2, line number 38, after infarction delete "compared,", insert --.--

At column 2, line number 41, after for delete "a", insert --an--

At column 2, line number 64, delete "(a)", insert --a)--

At column 2, line number 65, after methods of delete "to"

At column 3, line number 49, delete "know", insert --known--

At column 3, line number 56, after Ketaglutarate, insert --(--

At column 3, line number 63, after that delete "to"

At column 4, line number 4, after shown insert --to--

At column 4, line number 50, delete "fast-twice", insert --fast-twitch--

At column 5, line number 40, after that delete "to do", insert --do not--

In the claims:

At column 6, claim number 7, line number 8, after wherein delete "the"

At column 6, claim number 13, line number 39, after wherein delete "the"

Signed and Sealed this
Nineteenth Day of February, 2013

Teresa Stanek Rea
*Acting Director of the United States Patent and Trademark Office*